United States Patent
Seidelmann et al.

(10) Patent No.: US 6,818,661 B2
(45) Date of Patent: Nov. 16, 2004

(54) ANTHRANYLALKYL AND CYCLOALKYL AMIDES AND USE THEREOF AS VEGF RECEPTOR INHIBITORS

(75) Inventors: Dieter Seidelmann, Berlin (DE); Martin Krüger, Berlin (DE); Eckhard Ottow, Berlin (DE); Andreas Huth, Berlin (DE); Karl-Heinz Thierauch, Berlin (DE); Andreas Menrad, Oranienburg (DE); Martin Haberey, Berlin (DE)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 10/275,585

(22) PCT Filed: May 9, 2001

(86) PCT No.: PCT/EP01/05267

§ 371 (c)(1),
(2), (4) Date: May 9, 2003

(87) PCT Pub. No.: WO01/85691

PCT Pub. Date: Nov. 15, 2001

(65) Prior Publication Data

US 2003/0176469 A1 Sep. 18, 2003

(30) Foreign Application Priority Data

May 9, 2000 (DE) .......................................... 100 23 485

(51) Int. Cl.[7] ........................ C07D 213/00; A61K 31/44

(52) U.S. Cl. ....................................... 514/357; 546/336
(58) Field of Search ........................... 514/357; 546/336

(56) References Cited

U.S. PATENT DOCUMENTS 3,226,394 A * 12/1965 Schipper ..................... 546/337

FOREIGN PATENT DOCUMENTS

WO  WO 00/27819  * 3/2000  ......... C07D/213/38

\* cited by examiner

Primary Examiner—Zinna Northington Davis
(74) Attorney, Agent, or Firm—Lydia T. McNally; George R. Dohmann

(57) ABSTRACT

The invention relates to substituted anthranylalkyl and cycloalkyl amides of general formula (I) and to their use as medicaments for treating diseases caused by persistent angiogenesis.

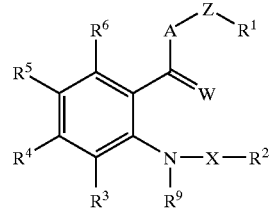

(I)

5 Claims, No Drawings

ANTHRANYLALKYL AND CYCLOALKYL AMIDES AND USE THEREOF AS VEGF RECEPTOR INHIBITORS

The invention relates to substituted anthranylalkyl and -cycloalkyl amides and their use as medicaments in the treatment of diseases caused by persistent angiogenesis.

Persistent angiogenesis may be the cause of various diseases such as psoriasis, arthritis, such as rheumatoid arthritis, haemangioma, angiofibroma, eye diseases such as diabetic retinopathy, neovascular glaucoma, kidney diseases such as glomerulonephritis, diabetic nephropathy, malignant nephrosclerosis, thrombic microangiopathic syndrome, transplantation rejections and glomerulopathy, fibrotic diseases such as cirrhosis of the liver, mesangial cell proliferation diseases, artheriosclerosis and injuries to nerve tissue, or may lead to a worsening of these diseases.

The direct or indirect inhibition of the VEGF receptor can be used to treat such diseases and other VEGF-induced pathological angiogenesis and vascular permeable conditions, such as tumour vascularisation. For example, it is known that the growth of tumours can be inhibited by soluble receptors and antibodies to VEGF.

Persistent angiogenesis is induced by the VEGF through its receptor. So that VEGF can display this activity, it is necessary for VEGF to bind to the receptor and for tyrosine phosphorylation to develop.

It has now been found that compounds of general formula I:

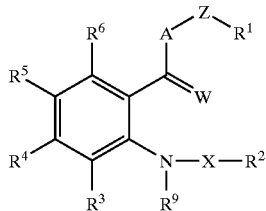

I in which

A is the group $=NR^7$,

W is oxygen, sulfur, two hydrogen atoms or the group $=NR^8$,

Z is a bond or the group $=NR^{10}$ or $=N-$, $R^1$ is branched or unbranched $C_{1-12}$-alkyl or $C_{2-12}$-alkenyl which is optionally substituted once or many times by halogen, hydroxy, $C_{1-6}$-alkyloxy, aralkyloxy, $C_{1-6}$-alkyl and/or $NR^{11}R^{12}$; or $C_{3-10}$-cycloalkyl, or $C_{3-10}$-cycloalkenyl which is optionally substituted once or many times by halogen, hydroxy, $C_{1-6}$-alkyloxy, aralkyloxy, $C_{1-6}$-alkyl and/or $NR^{11}R^{12}$, X is $C_{1-6}$-alkyl;

$R^2$ signifies monocyclic or bicyclic heteroaryl, which is unsubstituted or optionally substituted once or many times by halogen, $C_{1-6}$-alkyl, $C_{1-6}$-alkoxy and/or hydroxy, $R^3$, $R^4$, $R^5$ and $R^6$ are hydrogen, halogen; or $C_{1-6}$-alkoxy, $C_{1-6}$-alkyl, $C_{1-6}$-carboxyalkyl either unsubstituted or optionally substituted once or many times by halogen, $R^7$ is hydrogen, $C_{1-6}$-alkyl or $C_{1-8}$-cycloalkyl, $R^8$, $R^9$ and $R^{10}$ are hydrogen or $C_{1-6}$-alkyl and $R^{11}$ and $R^{12}$ are hydrogen or $C_{1-6}$-alkyl or form a ring which may contain a further hetero atom and may be optionally substituted by $C_{1-6}$-alkyl, as well as the isomers and salts thereof, stop tyrosine phosphorylation or persistent angiogenesis and thus prevent the growth and spread of tumours.

By alkyl is understood in each case a straight-chain or branched alkyl radical, such as methyl, ethyl, propyl, isopropyl, butyl, isobutyl, sec. butyl, tert.-butyl, pentyl, isopentyl or hexyl, heptyl, octyl, nonyl, decyl, undecyl, dodecyl.

By cycloalkyl is understood monocyclic alkyl rings, such as cyclopropyl, cyclobutyl, cyclopentyl, cyclohexyl oder cycloheptyl, cyclooctyl, cyclononyl or cyclodecyl, and also bicyclic rings or tricyclic rings, for example adamantanyl.

By cycloalkenyl is understood in each case cyclobutenyl, cyclopentenyl, cyclohexenyl, cycloheptenyl, cyclooctenyl, cyclononenyl or cyclodecenyl, whereby linking may take place at the double bond and also at the single bonds.

Halogen is understood to be in each case fluorine, chlorine, bromine or iodine.

The alkenyl substituents are respectively straight-chained or branched and contain 2–6, preferably 2–4 carbon atoms. The following radicals may be mentioned by way of example: vinyl, propen-1-yl, propen-2-yl, but-1-en-1-yl, but-1-en-2-yl, but-2-en-1-yl, but-2-en-2-yl, 2-methyl-prop-2-en-1-yl, 2-methyl-prop-1-en-1-yl, but-1-en-3-yl, but-3-en-1-yl, allyl.

The aryl radical respectively has 6–12 carbon atoms, for example naphthyl, biphenyl and in particular phenyl.

The heteroaryl radical may be respectively benzocondensed. Examples of 5-ring heteroaromatics are: thiophene, furan, oxazole, thiazole, imidazole, pyrazole and benzo derivatives, and examples of 6-ring heteroaromatics are pyridine, pyrimidine, triazine, quinoline, isoquinoline and benzo derivatives.

The aryl and the heteroaryl radical may respectively be substituted once, twice or three times by identical or different substituents from hydroxy, halogen, $C_{1-4}$-alkoxy.

If an acidic function is contained therein, suitable salts are the physiologically acceptable salts of organic and inorganic bases, for example the readily soluble alkali and alkaline earth salts, as well as N-methyl-glucamine, dimethyl glucamine, ethyl glucamine, lysine, 1,6-hexadiamine, ethanolamine, glucosamine, sarcosine, serinol, tri-hydroxy-methyl-amino-methane, amino-propanediol, Sovak base, 1-amino-2,3,4-butanetriol.

If a basic function is contained therein, suitable salts are the physiologically acceptable salts of organic and inorganic acids, such as hydrochloric acid, sulphuric acid, phosphoric acid, citric acid, tartaric acid, fumaric acid, etc.

Of particular interest are those compounds of the general formula I, in which

A is the group $=NR^7$,

W is oxygen,

Z is a bond, $R^1$ is branched or unbranched $C_{1-12}$-alkyl or $C_{2-12}$-alkenyl which is optionally substituted once or many times by halogen, hydroxy, $C_{1-6}$-alkyloxy, aralkyloxy, $C_{1-6}$-alkyl and/or $NR^{11}R^{12}$; or $C_{3-10}$-cycloalkyl, or $C_{3-10}$-cycloalkenyl which is optionally substituted once or many times by halogen, hydroxy, $C_{1-6}$-alkyloxy, aralkyloxy, $C_{1-6}$-alkyl and/or $NR^{11}R^{12}$, X is $C_{1-6}$-alkyl;

$R^2$ signifies monocyclic or bicyclic heteroaryl, which is unsubstituted or optionally substituted once or many times by halogen, $C_{1-6}$-alkyl, $C_{1-6}$-alkoxy and/or hydroxy, $R^3$, $R^4$, $R^5$ and $R^6$ are hydrogen, halogen; or $C_{1-6}$-alkoxy, $C_{1-6}$-alkyl, $C_{1-6}$-carboxyalkyl either unsubstituted or optionally substituted once or many times by halogen, $R^7$ is hydrogen, $C_{1-6}$-alkyl or $C_{1-8}$-cycloalkyl, $R^9$ is hydrogen or $C_{1-6}$-alkyl and $R^{11}$ and $R^{12}$ are hydrogen or $C_{1-6}$-alkyl or form a ring which may contain a further hetero atom and may be optionally substituted by $C_{16}$-alkyl, as well as the isomers and salts thereof.

Of particular interest are those compounds of the general formula I, in which

A is the group =$NR^7$,

W is oxygen,

Z is a bond, $R^1$ is branched or unbranched $C_{1-12}$-alkyl or $C_{2-12}$-alkenyl which is optionally substituted once or many times by halogen, hydroxy, $C_{1-6}$-alkyloxy, aralkyloxy, $C_{1-6}$-alkyl and/or $NR^{11}R^{12}$; or $C_{3-10}$-cycloalkyl, or $C_{3-10}$-cycloalkenyl which is optionally substituted once or many times by halogen, hydroxy, $C_{1-6}$-alkyloxy, aralkyloxy, $C_{1-6}$-alkyl and/or $NR^{11}R^{12}$, X is $C_{1-6}$-alkyl;

$R^2$ is pyridyl, $R^3$, $R^4$, $R^5$ and $R^6$ are hydrogen, halogen; or $C_{1-6}$-alkoxy, $C_{1-6}$-alkyl, $C_{1-6}$-carboxyalkyl either unsubstituted or optionally substituted once or many times by halogen, $R^7$ is hydrogen, $C_{1-6}$-alkyl or $C_{1-8}$-cycloalkyl, $R^9$ is hydrogen or $C_{1-6}$-alkyl and $R^{11}$ and $R^{12}$ are hydrogen or $C_{1-6}$-alkyl or form a ring which may contain a further hetero atom and may be optionally substituted by $C_{1-6}$-alkyl, as well as the isomers and salts thereof.

Of particular value are those compounds of the general formula I, in which

A is the group =$NR^7$,

W is oxygen,

Z is a bond, $R^1$ is branched or unbranched $C_{1-12}$-alkyl or $C_{2-12}$-alkenyl which is optionally substituted once or many times by halogen, hydroxy, $C_{1-6}$-alkyloxy, aralkyloxy, $C_{1-6}$-alkyl and/or $NR^{11}R^{12}$; or $C_{3-10}$-cycloalkyl, or $C_{3-10}$-cycloalkenyl which is optionally substituted once or many times by halogen, hydroxy, $C_{1-6}$-alkyloxy, aralkyloxy, $C_{1-6}$-alkyl and/or $NR^{11}R^{12}$, X is $C_{1-6}$-alkyl;

$R^2$ is pyridyl, $R^3$, $R^4$, $R^5$ and $R^6$ are hydrogen, halogen; or $C_{1-6}$-alkoxy, $C_{1-6}$-alkyl, $C_{1-6}$-carboxyalkyl either unsubstituted or optionally substituted once or many times by halogen, $R^7$ is hydrogen, $C_{1-6}$-alkyl or $C_{1-8}$-cycloalkyl, $R^9$ is hydrogen or $C_{1-6}$-alkyl and $R^{11}$ and $R^{12}$ are hydrogen or $C_{1-6}$-alkyl, or form a ring which may contain oxygen or nitrogen as a further hetero atom and may be optionally substituted by $C_{1-6}$-alkyl, as well as the isomers and salts thereof.

The compounds of the general formula I which have proved to be especially valuable are those in which A is the group =$NR^7$, W is oxygen, Z is a bond, $R^1$ is branched or unbranched $C_{1-12}$-alkyl which is optionally substituted once or many times by halogen, $C_{1-6}$-alkyloxy or $NR^{11}R^{12}$; or $C_{3-10}$-cycloalkyl which is optionally substituted once or many times by hydroxy, $C_{1-6}$-alkyloxy, $C_{1-6}$-alkyl or benzyloxy, X is $C_{1-6}$-alkyl;

$R^2$ is pyridyl, $R^3$, $R^4$, $R^5$ and $R^6$ are hydrogen, $R^7$ and $R^9$ are hydrogen, $R^{11}$ and $R^{12}$ are hydrogen or $C_{1-6}$-alkyl or form a morpholinyl, piperidinyl, pyrrolidinoyl or tetrahydrofuranyl ring, which may be optionally substituted by $C_{1-6}$-alkyl, as well as the isomers and salts thereof.

The compounds according to the invention prevent phosphorylation, i.e. certain tyrosine kinases can be selectively inhibited, whereby the persistent angiogenesis can be stopped. In this way, for example, the growth and spread of tumours is suppressed.

The compounds of the general formula I according to the invention also contain the possible tautomeric forms and include the E- or Z-isomers, or if a chiral centre is present, also the racemates and enantiomers.

Owing to their inhibitory activity in respect of phosphorylation of the VEGF receptor, the compounds of formula I and their physiologically acceptable salts may be used as medicaments. Owing to their profile of activity, the compounds according to the invention are suitable for treating diseases caused by or accelerated by persistent angiogenesis.

Since the compounds of formula I are identified as inhibitors of KDR and FLT tyrosine kinase, they are especially suitable for treating those diseases that are caused by or accelerated by the persistent angiogenesis, triggered by the VEGF receptor, or by an increase in vascular permeability.

The object of the present invention is also the use of the compounds according to the invention as inhibitors of KDR and FLT tyrosine kinase.

A further object of the present invention is thus the medicaments for treating tumours, and their use.

The compounds according to the invention may be used either on their own or in a formulation as a medicament for treating psoriasis, arthritis, such as rheumatoid arthritis, haemangioma, angiofibroma, eye diseases such as diabetic retinopathy, neovascular glaucoma, kidney diseases such as glomerulonephritis, diabetic nephropathy, malignant nephrosclerosis, thrombic microangiopathic syndrome, transplantation rejections and glomerulopathy, fibrotic diseases such as cirrhosis of the liver, mesangial cell proliferation diseases, artheriosclerosis and injuries to nerve tissue.

When treating injuries to nerve tissue, the compounds according to the invention can prevent rapid formation of scar tissue at the site of the wounds, i.e. the onset of scar formation is prevented before the axons join together again. Thus, reconstruction of the nerve unions is simplified.

In addition, the compounds according to the invention suppress ascites formation in patients. Similarly, VEGF-induced oedema are suppressed.

Such medicaments, their formulations and uses are likewise objects of the present invention.

The invention further relates to the use of the compounds of the general formula I in the production of a medicament for treating tumours, psoriasis, arthritis, such as rheumatoid arthritis, haemangioma, angiofibroma, eye diseases such as diabetic retinopathy, neovascular glaucoma, kidney diseases such as glomerulonephritis, diabetic nephropathy, malignant nephrosclerosis, thrombic microangiopathic syndrome, transplantation rejections and glomerulopathy, fibrotic diseases such as cirrhosis of the liver, mesangial cell proliferation diseases, artheriosclerosis and injuries to nerve tissue.

When using the compounds of formula I as medicaments, they are brought into the form of a pharmaceutical preparation, which contains, in addition to the active ingredient for enteral or parenteral application, appropriate pharmaceutical, organic or inorganic inert carriers, for example water, gelatin, gum arabic, lactose, starch, magnesium stearate, talc, vegetable oils, polyalkylene glycols etc. The pharmaceutical preparations may exist in solid form, for example as tablets, coated tablets, suppositories, capsules, or in liquid form, for example as solutions, suspensions or emulsions. They may additionally contain excipients such as preservatives, stabilizers, wetting agents or emulsifiers, salts to change the osmotic pressure or buffers.

For parenteral application, injection solutions or suspensions are especially suitable, particularly aqueous solutions of the active compounds in polyhydroxy-ethoxylated castor oil.

Surface-active excipients may also be used as carrier systems, for example salts of bile acid or animal or vegetable phospholipids, and also mixtures thereof, as well as liposomes or constituents thereof.

For oral application, tablets, coated tablets or capsules are especially suitable, with talcum and/or hydrocarbon carriers or binders, for example lactose, corn starch or potato starch. Application may also be carried out in liquid form, for example as juice, to which a sweetener and/or a flavouring agent may optionally be added.

Dosaging of the active ingredients may vary according to the mode of administration, the age and the weight of the patient, the nature and severity of the illness to be treated and similar factors. The daily dose is 0.5–1000 mg, preferably 50–200 mg, whereby the dose may be given as a single dose to be administered once or may be divided into two or more daily doses. The above-described formulations and dosage forms are likewise objects of the present invention.

Preparation of the compounds according to the invention is carried out according to known methods. For example, the compounds of formula I are obtained, whereby a) in a compound of formula II:

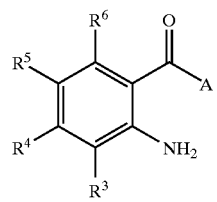

II wherein $R^3$ to $R^6$ are defined as above and A is $OR^{13}$, whereby $R^{13}$ is hydrogen or $C_{1-4}$-alkyl or $C_{1-4}$-acyl, first of all the amine is alkylated and then COA is converted into an amide, or b) in a compound of formula III:

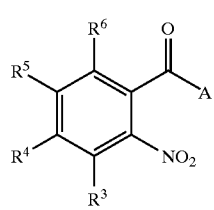

III wherein $R^3$ bis $R^6$ are defined as above, and A is halogen or $OR^{13}$, whereby $R^{13}$ may be hydrogen, lower alkyl or acyl, COA is converted into an amide, the nitro group is reduced to the amine and is then alkylated, In all cases, the sequence of steps can be switched.

Amide formation is effected according to methods known in literature.

An amide may be formed from a corresponding ester. The ester is reacted in accordance with J. Org. Chem. 1995, 8414 with aluminium trimethyl and the corresponding amine in solvents such as toluene at temperatures of 0° C. to boiling point of the solvent. If the molecule contains two ester groups, both are converted to the same amide.

When using nitriles instead of the ester, amidines are obtained under analogous conditions.

To form the amide, all methods that are known from peptide chemistry may be used. For example, the corresponding acid can be reacted with the amine in aprotic polar solvents, for example dimethylformamide via an activated acid derivative, for example obtainable with hydroxybenzotriazole and a carbodiimide, such as diisopropyl carbodiimide, or also with prepared reagents, for example HATU (Chem. Comm. 1994, 201) or BTU, at tempertures between 0° C. and boiling point of the solvent. To form the amide, the method using the mixed acid anhydride, the acid chloride, the imidazolide or the azide may also be employed. For reactions of the acid chloride, the solvent dimethyl acetamide is preferred at temperatures from room temperature to boiling point of the solvent, preferably 80–100° C.

If different amide groups are to be introduced into the molecule, the second ester group must be introduced into the molecule for example after producing the first amide group, and is then amidated, or a molecule exists in which one group is present as an ester and the other as an acid, and the two groups are amidated after each other by different methods.

Thioamides may be obtained from the anthranilamides by a reaction with diphosphadithianes according to Bull Soc. Chim. Belg. 87, 229, 1978 or by a reaction with phosphorus pentasulfide in solvents such as pyridine or also without any solvents at all at temperatures of 0° C. to 200° C.

Reduction of the nitro group is carried out in polar solvents at room temperature or at elevated temperature. Suitable catalysts for reduction are metals such as Raney nickel or noble metal catalysts such as palladium or platinum or also palladium hydroxide, optionally on carriers. Instead of hydrogen, ammonium formate, cyclohexene or hydrazine may also be used, for example, in known manner. Reducing agents such as tin II chloride or titanium (III) chloride may be used in the same way as complex metal hydrides, optionally in the presence of heavy metal salts. Iron may also be used as a reducing agent. In this case, the reaction is carried out in the presence of an acid, such as acetic acid or ammonium chloride, optionally adding a solvent, for example water, methanol, iron/ammonia etc. In the prolonged reaction time in this variant, acylation of the amino group can occur.

If alkylation of an amino group is desired, alkylation may be effected by the usual methods—for example with alkyl halides—or by the Mitsonubo variant by a reaction with an alcohol in the presence of for example triphenylphosphine and azodicarboxylic acid ester. The amine may also undergo reductive alkylation with aldehydes or ketones, whereby the reaction is carried out in the presence of a reducing agent, for example sodium cyanoborohydride in a suitable inert solvent, for example ethanol, at temperatures from 0° C. to boiling point of the solvent. When starting with a primary amino group, the reaction is effected optionally with two different carbonyl compounds after one another, whereby mixed derivatives are obtained [literature e.g. Verardo et al. Synthesis (1993), 121; Synthesis (1991), 447; Kawaguchi, Synthesis (1985), 701; Micovic et al. Synthesis (1991), 1043].

It may also be advantageous to firstly form the Schiff's base by reacting the aldehyde with the amine in solvents such as ethanol or methanol, optionally adding excipients such as glacial acetic acid, and only then to add reducing agents, e.g. sodium cyanoborohydride.

Ether cleavages are carried out by conventional methods known from literature. Here, even if several groups are present in the molecule, selective cleavage can be achieved. The ether is treated for example with boron tribromide in solvents such as dichloromethane at temperatures between −10° C. and boiling point of the solvent, preferably at −78°

C. However, it is also possible to cleave the ether by means of sodium thiomethylate in solvents such as dimethylformamide. The temperature may be between room temperature and boiling point of the solvent, preferably 150° C. In the case of benzyl ethers, cleavage is also effected with strong acids, for example trifluoroacetic acid, at temperatures from room temperature to boiling point, preferably at 70° C.

The isomeric mixtures can be separated by conventional methods, for example crystallisation, any form of chromatography or by salt formation, into the enantiomers or E/Z-isomers.

Production of the salts takes place in conventional manner, by mixing a solution of the compound of formula I with the equivalent amount or with an excess of a base or acid, which is optionally in solution, and separating the precipitate or by working up the solution in conventional manner.

The following examples illustrate the preparation of the compounds according to the invention without limiting the scope of the compounds being claimed to these examples.

EXAMPLE 1.0

N-(4-methylcyclohexyl)-2-(4-pyridylmethyl)amino) benzoic acid amide 849 mg (7.5 mmols) of 4-methylcyclohexylamine (cis/trans mixture) are placed in 7.5 ml of toluene under argon, whilst excluding moisture and cooling with ice, and are mixed dropwise with 4.5 ml of a trimethyl aluminium solution (2.5 M in toluene). Subsequently, a cold solution of 1.21 g (5 mmols) of N(4-pyridylmethyl)anthranylic acid methyl ester in 10 ml of toluene is added, the ice cooling is stopped, stirring is effected for 10 mins at room temperature and the mixture is then boiled under reflux for 1 h. After cooling, it is added to a saturated sodium carbonate solution and extracted with ethyl acetate. The ethyl acetate phase is washed with water and saturated sodium chloride solution, dried, filtered and concentrated. The residue is chromatographed over silica gel with hexane:ethyl acetate=4:6 as eluant. 1.45 g (90% of theory) of a cis/trans mixture of N-(4-methylcyclohexyl)-2-(4-pyridylmethyl)amino)benzoic acid amide are obtained.

The following compounds are also produced in analogous manner:

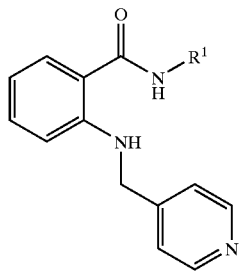

| Example | $R^1$ | melting point ° C. |
|---|---|---|
| 1.1 | ▷ cyclopropylmethyl | 130–131 |
| 1.2 | cyclohexyl | 128.6 |
| 1.3 | cyclohexylmethyl | 116 |
| 1.4 | cyclooctyl | 103–104 |
| 1.5 | 4-methylcyclohexyl (Me) | 93–95 |

-continued
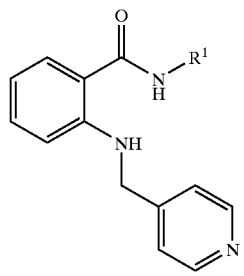
| Example | R¹ | melting point ° C. |
|---|---|---|
| 1.6 | (1-methylcyclohexyl)methyl | oil |
| 1.7 | (2,6-dimethylcyclohexyl)methyl | 93–94 |
| 1.8 | (4-t-butylcyclohexyl)methyl | 118.4 |
| 1.9 | adamantylmethyl | 102.5 |
| 1.10 | n-propyl | 85 |
| 1.11 | n-butyl | |
| 1.12 | n-hexyl | |
| 1.13 | n-octyl | oil |
| 1.14 | n-decyl | |
| 1.15 | n-dodecyl | 84.8 |
| 1.16 | isobutyl | 121.6 |
| 1.17 | 2-methylbutyl | |
| 1.18 | neopentyl | |

-continued
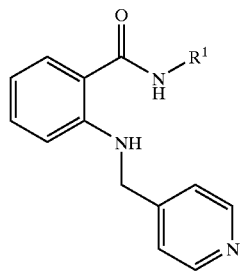
| Example | R¹ | melting point ° C. |
|---|---|---|
| 1.19 | neopentyl-CH₂- | |
| 1.20 | isobutyl-CH₂- | oil |
| 1.21 | sec-butyl- | |
| 1.22 | -CH₂-C(CH₃)₂-CH₂CH₃ (approx) | 104.6 |
| 1.23 | -CH₂-CH(CH₃)-CH₂-CH(CH₃) | |
| 1.24 | -(CF₂)₂-CF₃ | oil |
| 1.25 | -(CF₂)₆-CF₃ | 110–11 |
| 1.26 | -CH₂CH₂-morpholinyl | 106.2 |
| 1.27 | -CH₂CH₂-piperidinyl | 65.2 |
| 1.28 | -CH₂CH₂-pyrrolidinyl | 103–105 |
| 1.29 | -CH₂CH₂-N(CH₃)₂ | oil |
| 1.30 | -CH₂CH₂CH₂-OMe | oil |

EXAMPLE 2.0

2-(N(4-pyridylmethyl)aminobenzoic acid-(1S,2S)-(−)-benzyloxycyclohexylamide 684 mg (3 mmols) of N(4-pyridylmethyl)anthranylic acid are dissolved in 18 ml of dimethylformamide and mixed under argon, whilst excluding moisture, with 405 mg (3 mmols) of hydroxybenzotriazole, 573 mg (3 mmols) of N-(3-dimethylaminopropyl)-N-ethylcarbodiimide hydrochloride, 615 mg (3 mmols) of (1S,2S)-(−)-benzyloxycyclohexylamine and 774 mg (6 mmols) of N-ethyidiisopropylamine and stirred for 2 h at 80° C. bath temperature. After concentrating under vacuum, the residue is taken up in 50 ml of diluted sodium hydrogen carbonate solution and shaken out three times with 50 ml of ethyl acetate. The combined organic phase is washed with water, dried, filtered and concentrated. The residue is chromatographed over silica gel with methylene chloride:ethanol=10:1 as eluant. 530 mg (=42.4% of theory) of 2-(N(4-pyridylmethyl)aminobenzoic acid-(1S,2S)-(−)-benzyloxycyclohexylamide are obtained with a melting point of 121.9° C.

The following compound is also produced in analogous manner:

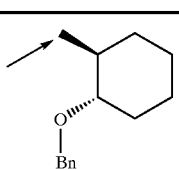

| Example | R¹ | melting point ° C. |
|---|---|---|
| 2.1 | | 125.1 |

Bn = Benzyl

EXAMPLE 3.0

2-(N(4-pyridylmethyl)aminobenzoic acid-(1S,2S)-(−)-hydroxycyclohexylamide 250 mg (0.6 mmols) of pyridylmethyl)aminobenzoic acid-(1S,2S)-(−)-benzyloxycyclohexylamide are added to 2 ml of trifluoroacetic acid and heated for 2 h at 80° C. After concentrating under vacuum, it is taken up in 50 ml of diluted sodium hydrogen carbonate solution and extracted three times with 50 ml of ethyl acetate. The combined organic phase is washed with water, dried, filtered and concentrated. The residue is chromatographed over silica gel with acetone:hexane=1:1 as eluant. 76 mg (=48% of theory) of 2-(N(4-pyridylmethyl)aminobenzoic acid-(1S,2S)-(−)-hydroxycyclohexylamide are obtained with a melting point of 141.5° C.

The following compound is also produced in analogous manner:

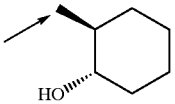

| Example | R¹ | melting point ° C. |
|---|---|---|
| 3.1 | | 161.1 |

Purification of the Compounds

HPLC separation of the cis/trans mixture of N-(4-methylcyclohexyl)-2-(4-pyridylmethyl)amino)benzoic. acid amide of example 1

140 mg of a cis/trans mixture of N-(4-methylcyclohexyl)-2-(4-pyridylmethyl)amino)benzoic acid amide are separated through a Chiralpak AD column with hexane:EtOH=85:15 at a flow rate of 30 ml/min. 15.9 mg of cis-N-(4-methylcyclohexyl)-2-(4-pyridylmethyl)amino)-benzoic acid amide are obtained with a retention time of 15 mins, and 21.5 mg of trans-N-(4-methylcyclohexyl)-2-(4-pyridylmethyl)amino)-benzoic acid amide are obtained with a retention time of 19 mins.

Preparation of the Intermediates

Insofar as the production of the intermediates is not described, these are known or may be produced analogously to known compounds or analogously to the processes described here. The intermediates described are especially suitable for the production of the anthranylalkyl and -cycloalkyl amides according to the invention.

The intermediates are partly self-active and may therefore similarly be used in the production of a medicament for treating tumours, psoriasis, arthritis, such as rheumatoid arthritis, haemangioma, angiofibroma, eye diseases such as diabetic retinopathy, neovascular glaucoma, kidney diseases such as glomerulonephritis, diabetic nephropathy, malignant nephrosclerosis, thrombic microangiopathic syndrome, transplantation rejections and glomerulopathy, fibrotic diseases such as cirrhosis of the liver, mesangial cell proliferation diseases, artheriosclerosis and injuries to nerve tissue, for stopping ascites formation and for suppressing VEGF-induced oedema.

The following examples illustrate the preparation of the intermediates according to the invention which are especially suitable for producing the compounds of general formula I according to the invention, without limiting the invention to these examples.

A N(4-pyridylmethyl)anthranylic acid methyl ester 15.1 g (100 mmols) of anthranilic acid methyl ester in 600 ml of methanol are mixed with 6 ml of glacial acetic acid and 17.2 g (160 mmols) of 4-pyridine-carbaldehyde and stirred for 12 h at room temperature. Then, whilst cooling in an ice bath, 11.4 g (160 mmols) of sodium cyanoborohydride are added and stirred for 12 h at room temperature. The preparation is rotated, the residue taken up in 500 ml of ethyl acetate, and washed in succession with saturated sodium hydrogen carbonate solution and saturated sodium chloride solution. The crude product is chromatographed over silica gel with acetone:hexane=1:1 as eluant. After combining the corresponding fractions and stirring with hexane:ethyl acetate=8:2, 15.7 g (65% of theory) of N-(4-pyridylmethyl)-anthranylic acid methyl ester are obtained.

B N(4-pyridylmethyl)anthranylic acid 2 g (8.3 mmols) of N-(4-pyridylmethyl)anthranylic acid methyl ester are mixed in 15 ml of methanol with 16 ml (16 mmols) of a 1 N sodium hydroxide solution and boiled at reflux for 1 h. After drawing off the methanol in a vacuum, 20 ml of water and 20 ml of a 1 M citric acid are added, the precipitate is filtered by suction, washed with water and dried over phosphorus pentoxide. 1.7 g (90% of theory) of N-(4-pyridylmethyl)anthranylic acid are obtained with a melting point of 208° C.

The following application examples illustrate the biological activity and use of the compounds according to the invention without limiting them to the examples.
Solutions Required for the Tests
Stock Solutions
Stock solution A: 3 mM ATP in water pH 7.0 (−70° C.)
Stock solution B: g-33P-ATP 1 mCi/100 µl
Stock solution C: poly-(Glu4Tyr) 10 mg/ml in water
Solution for dilutions
Substrate solvent: 10 mM DTT, 10 mM manganese chloride 100 mM magnesium chloride
Enzyme solution: 120 mM Tris/HCl, pH 7.5, 10 µM sodium vanadium oxide Application Example 1

Inhibition of KDR- and FLT-1 kinase activity in the presence of the compounds according to the invention 10 µl of substrate mix [10 µl vol ATP stock solution A+25 µCi g-33P-ATP (ca. 2.5 µl of stock solution B)+30 µl poly-(Glu4Tyr) stock solution C+1.21 ml substrate solvent], 10 µl inhibitor solution [substances corresponding to the dilutions, as a control 3% DMSO in substrate solvent] and 10 µl enzyme solution [11.25 µg enzyme stock solution (KDR or FLT-1 kinase) are diluted at 4° C. in 1.25 ml enzyme solution], are added to a tapering microtitre plate (without protein binding). The mixture is mixed thoroughly and incubated for 10 minutes at room temperature. Subsequently, 10 µl of stop solution (250 mM EDTA, pH 7.0) is added, mixed and 10 µl of the solution transferred to a P 81 phosphocellulose filter. It is subsequently washed several times in 0.1M phosphoric acid. The filter paper is dried, coated with MeltiLex and measured in a MicroBeta counter.

The IC50 values are determined from the concentration of inhibitor required to inhibit the phosphate incorporation to 50% of the uninhibited incorporation after deducting the reference value (EDTA-stopped reaction).

The results of the kinase inhibition IC50 in µM are illustrated in the following table.

| Example No. | VEGFR I (FLT) | VEGFR II (KDR, nM) |
|---|---|---|
| 1.8 | 500 | 39 |
| 1.14 | 200 | 200 |
| 1.23 | 400 | 500 |
| 1.19 | 200 | 50 |

-continued

| Example No. | VEGFR I (FLT) | VEGFR II (KDR, nM) |
|---|---|---|
| 1.4 | 100 | 80 |
| 1.27 | 2000 | 1000 |

What we claim is:
1. A compound of the formula:

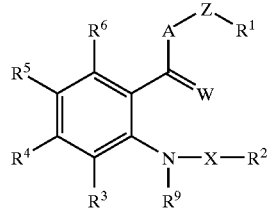

in which
A is the group —NR$^7$;
W is oxygen or sulfur;
Z is a bond;
R$^1$ is C$_{3-10}$cycloalkyl, or C$_{3-10}$cycloalkenyl which is optionally substituted once or many times by halogen, hydroxy, C$_{1-6}$alkyloxy, aralkyloxy, C$_{1-6}$alkyl and/or NR$^{11}$R$^{12}$;
X is C$_{1-6}$alkyl;
R$^2$ is pyridyl;
R$^3$, R$^4$, R$^5$ and R$^6$ are hydrogen, halogen; or C$_{1-6}$alkoxy, C$_{1-6}$alkyl, C$_{1-6}$carboxyalkyl either unsubstituted or optionally substituted once or many times by halogen;
R$^7$ is hydrogen, C$_{1-6}$alkyl or C$_{1-8}$cycloalkyl;
R$^8$, R$^9$ and R$^{10}$ are hydrogen or C$_{1-6}$alkyl; and
R$^{11}$ and R$^{12}$ are hydrogen or C$_{1-6}$alkyl or form a ring which may contain a further hetero atom and may be optionally substituted by C$_{1-6}$alkyl,
except those compounds, in which
W is oxygen;
Z is a bond;
X is C$_2$alkyl;
R$^2$ signifies unsubstituted 4-pyridyl;
R$^3$, R$^4$, R$^6$, R$^7$ and R$^9$ are, respectively, hydrogen;
R$^5$ is hydrogen or chlorine; and
R$^1$ signifies n-propyl, cyclopropyl or allyl, and isomers and salts thereof.

2. A compound of formula (I), according to claim 1 in which:
A is the group —NR$^7$;
W is oxygen;
Z is a bond;
R$^1$ is C$_{3-10}$cycloalkyl, or C$_{3-10}$cycloalkenyl which is optionally substituted once or many times by halogen, hydroxy, C$_{1-6}$alkyloxy, aralkyloxy, C$_{1-6}$alkyl and/or NR$^{11}$R$^{12}$;
X is C$_{1-6}$alkyl;
R$^2$ is pyridyl;
R$^3$, R$^4$, R$^5$ and R$^6$ are hydrogen, halogen; or C$_{1-6}$alkoxy, C$_{1-6}$alkyl, C$_{1-6}$carboxyalkyl either unsubstituted or optionally substituted once or many times by halogen;

$R^7$ is hydrogen, $C_{1-6}$alkyl or $C_{1-8}$cycloalkyl;

$R^9$ is hydrogen or $C_{1-6}$alkyl; and $R^{11}$ and $R^{12}$ are hydrogen or $C_{1-6}$alkyl or form a ring which may contain a further hetero atom and may be optionally substituted by $C_{1-6}$alkyl, and the isomers and salts thereof.

3. A compound of formula (I), according to claim 1, in which:

A is the group —$NR^7$;

W is oxygen;

Z is a bond;

$R^1$ is $C_{3-10}$cycloalkyl, or $C_{3-10}$cycloalkenyl which is optionally substituted once or many times by halogen, hydroxy, $C_{1-6}$alkyloxy, aralkyloxy, $C_{1-6}$alkyl and/or $NR^{11}R^{12}$;

X is $C^{1-6}$alkyl;

$R^2$ is pyridyl, $R^3$, $R^4$, $R^5$ and $R^6$ are hydrogen, halogen; or $C_{1-6}$alkoxy, $C_{1-6}$alkyl, $C_{1-6}$carboxyalkyl either unsubstituted or optionally substituted once or many times by halogen;

$R^7$ is hydrogen, $C_{1-6}$alkyl or $C_{1-8}$cycloalkyl;

$R^9$ is hydrogen or $C_{1-6}$alkyl; and $R^{11}$ and $R^{12}$ are hydrogen or $C_{1-6}$alkyl, or form a ring which may contain oxygen or nitrogen as a further hetero atom and may be optionally substituted by $C_{1-6}$alkyl, and the isomers and salts thereof.

4. A compound of formula (I), according to claim 1, in which:

A is the group —$NR^7$;

W is oxygen;

Z is a bond;

$R^1$ is branched or unbranched $C_{1-12}$alkyl which is optionally substituted once or many times by halogen, $C_{1-6}$alkyloxy or $NR^{11}R^{12}$; or $C_{3-10}$cycloalkyl which is optionally substituted once or many times by hydroxy, $C_{1-6}$alkyloxy, $C_{1-6}$alkyl or benzyloxy;

X is $C_{1-6}$alkyl;

$R^2$ is pyridyl;

$R^3$, $R^4$, $R^5$ and $R^6$ are hydrogen;

$R^7$ and $R^9$ are hydrogen; and $R^{11}$ and $R^{12}$ are hydrogen or $C_{1-6}$alkyl or form a morpholinyl, piperidinoyl or pyrrolidinoyl ring, which may be optionally substituted by $C_{1-6}$alkyl, and the isomers and salts thereof.

5. A pharmaceutical composition comprising at least one compound according to claim 1 and a pharmaceutically acceptable carrier.

* * * * *